US012616758B2

(12) United States Patent
Lassus et al.

(10) Patent No.: US 12,616,758 B2
(45) Date of Patent: May 5, 2026

(54) FREEZE-DRIED COMPOSITION FOR PREPARING CALIBRATED GAS-FILLED MICROVESICLES

(71) Applicant: Bracco Suisse SA, Cadempino (CH)

(72) Inventors: Anne Lassus, Veyrier (CH); Samir Cherkaoui, Feigeres (FR)

(73) Assignee: Bracco Suisse SA, Cadempino (CH)

( * ) Notice: Subject to any disclaimer, the term of this patent is extended or adjusted under 35 U.S.C. 154(b) by 1054 days.

(21) Appl. No.: 17/620,170

(22) PCT Filed: Jun. 24, 2020

(86) PCT No.: PCT/EP2020/067756
§ 371 (c)(1),
(2) Date: Dec. 17, 2021

(87) PCT Pub. No.: WO2020/260423
PCT Pub. Date: Dec. 30, 2020

(65) Prior Publication Data
US 2022/0409749 A1 Dec. 29, 2022

(30) Foreign Application Priority Data

Jun. 25, 2019 (EP) .................................... 19182226

(51) Int. Cl.
| | |
|---|---|
| *A61K 9/19* | (2006.01) |
| *A61K 47/10* | (2017.01) |
| *A61K 47/26* | (2006.01) |
| *A61K 49/22* | (2006.01) |

(52) U.S. Cl.
CPC .............. *A61K 49/223* (2013.01); *A61K 9/19* (2013.01); *A61K 47/10* (2013.01); *A61K 47/26* (2013.01)

(58) Field of Classification Search
CPC ........ A61K 49/223; A61K 9/19; A61K 47/10; A61K 47/26
See application file for complete search history.

(56) References Cited

U.S. PATENT DOCUMENTS

| | | | |
|---|---|---|---|
| 10,918,605 | B2 | 2/2021 | Segers et al. |
| 2002/0159951 | A1 | 10/2002 | Unger et al. |
| 2003/0003055 | A1 | 1/2003 | Unger et al. |
| 2003/0175211 | A1 | 9/2003 | Schneider et al. |
| 2006/0034770 | A1 | 2/2006 | Schneider et al. |
| 2009/0274628 | A1 | 11/2009 | Ottoboni et al. |
| 2011/0045095 | A1 | 2/2011 | Hettiarachchi et al. |
| 2016/0158387 | A1 * | 6/2016 | Khnadhar .......... A61K 41/0052 600/12 |
| 2017/0080113 | A1 | 3/2017 | Henriksen et al. |
| 2018/0008951 | A1 | 1/2018 | Hoeve et al. |
| 2021/0000984 | A1 | 1/2021 | Segers et al. |

FOREIGN PATENT DOCUMENTS

| | | | | |
|---|---|---|---|---|
| CN | 105999314 | A | 10/2016 | |
| WO | 1995016467 | A1 | 6/1995 | |
| WO | 9729782 | A1 | 8/1997 | |
| WO | WO-2004069284 | A2 * | 8/2004 | ........... A61K 49/223 |
| WO | 2006018433 | A1 | 2/2006 | |
| WO | 2013141695 | A1 | 9/2013 | |
| WO | WO-2018041906 | A1 * | 3/2018 | ........... A61K 49/226 |
| WO | 2019170606 | A1 | 9/2019 | |
| WO | 2020260420 | A1 | 12/2020 | |

OTHER PUBLICATIONS

Cander, L., "Solubility of inert gases in human lung tissue," J. Appl. Physiol., 14(4):538-540 (1959).
Seo et al., "Size reduction of cosolvent-infused microbubbles to form acoustically responsive monodisperse perfluorocarbon nanodroplets," Lab Chip, 15:3581-3590 (2015).
Castro-Hernández, et al., "Microbubble generation in a co-flow device operated in a new regime", Lab. Chip., 11:2023-9 (2011).
International Search Report and Written Opinion for PCT/EP2020/067756, mailed Dec. 10, 2020.
Segers et al., "Stability of monodisperse phospholipid-coated microbubbles formed by flow-focusing at high production rates," Langmuir 32(16), 3937-3944 (2016).
Shih et al., "Flow-focusing regimes for accelerated production of monodisperse drug-loadable microbubbles toward clinical-scale applications," Lab. Chip, 13:4816-4826 (2013).
Sorgi, Frank L. et al., "Large scale production of DC-Chol cationic liposomes by microfluidization", International Journal of Pharmaceutics, 1996, vol. 144, pp. 131-139, Elsevier Science BV.
Utada, Andrew S. et al., "Dripping to Jetting Transitions in Coflowing Liquid Streams", Physical Review Letters, Aug. 31, 2007, vol. 99, pp. 094502-1-094502-4, The American Physical Society.
Van Hoeve, Wim et al., "Microbubble formation and pinch-off scaling exponent in flow-focusing devices", Physics of Fluids, 2011, vol. 23, pp. 092001-1-092001-8, American Institute of Physica.
Hettiarachchi, et al. "On-chip generation of microbubbles as a practical technology for manufacturing contrast agents for ultrasonic imaging," Lab Chip, 7:463-468 (2007).

* cited by examiner

*Primary Examiner* — Michael G. Hartley
*Assistant Examiner* — Samantha L Mejias
(74) *Attorney, Agent, or Firm* — VIVICAR Law, PLLC

(57) ABSTRACT

The present invention generally relates to the field of ultrasound contrast-agents (USCA). In particular, it relates to a freeze-dried composition comprising an amphiphilic material and a mixture of freeze-drying protecting components, which may be reconstituted for preparing a suspension of gas-filled microvesicles with calibrated size, useful in diagnostic or therapeutic applications. It further relates to the method for the preparation of such freeze-dried composition.

17 Claims, 2 Drawing Sheets

FREEZE-DRIED COMPOSITION FOR PREPARING CALIBRATED GAS-FILLED MICROVESICLES

CROSS-REFERENCE TO RELATED APPLICATIONS

Figure 1:
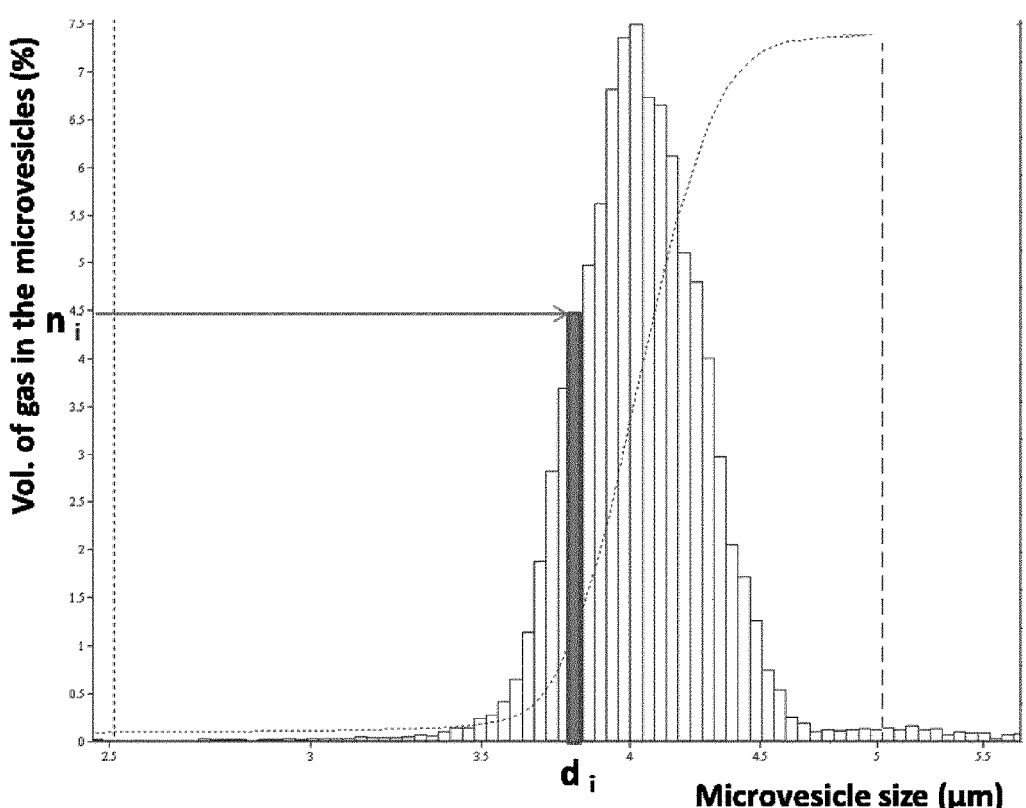

This application is the national stage application of corresponding international application number PCT/EP2020/067756, filed Jun. 24, 2020, which claims priority to and the benefit of European application no. 19182226.1, filed Jun. 25, 2019, which is hereby incorporated by reference in its entirety.

TECHNICAL FIELD

The present invention generally relates to the field of ultrasound contrast-agents (USCA). In particular, it relates to a freeze-dried composition comprising an amphiphilic material and a mixture of freeze-drying protecting components, which may be reconstituted for preparing a suspension of gas-filled microvesicles with calibrated size, useful in diagnostic or therapeutic applications. It further relates to the method for the preparation of such freeze-dried composition.

BACKGROUND OF THE INVENTION

Calibrated-size microvesicles (CMV) are a new generation of gaseous microbubbles having a narrow calibrated and controlled size distribution (mean sizes between 3 and 8 μm) compared to commercially available polydisperse microbubble ultrasound contrast-agents (USCA). These calibrated-size microbubbles are designed to enhance imaging sensitivity and improve efficiency to deliver drug and gene to specific organs. Calibrated microvesicles can be produced using various techniques: decantation, mechanical filtration, centrifugation, bubble sorting and flow-focusing. Particularly, the flow-focusing technology allows the manufacturing of calibrated microvesicles (typically with a geometric standard deviation (GSD) values between 1.05 and 1.08) in a highly reproducible way at a reasonable production rate (~60 million bubbles per minute), with acceptable concentrations of suspended microvesicles (e.g. between $3 \times 10^8$ CMV/mL and $4 \times 10^8$ CMV/mL) for subsequent uses.

Ref.1 [WO2018/041906 A1—BRACCO SUISSE SA] and Ref.2 [PCT application number PCT/EP2019/055325], both in the name of the Applicant, describe a method for preparing CMV, such as gas-filled microbubbles, in particular by using microfluidic technique.

Notwithstanding aqueous suspensions of calibrated microvesicles are highly stable at room temperature for few weeks, this stability may pose some constraints for a pharmaceutical product development, for which longer shelf life is generally desirable. There is thus a need to develop a long-term storage procedure. Freeze-drying, also known as lyophilization, is a complex and challenging process, widely used in the pharmaceutical industry that has the advantage of preserving pharmaceutical products under a dry form over several months. In fact, freeze-dried products display greater storage stability and can be easily shipped. Freeze-drying is also used in the field of gas filled microvesicles for preparing freeze-dried dosage forms which are then reconstituted with an aqueous solvent in the presence of a gas, to form a suspension of gas-filled microvesicles.

Ref3 [US2017/080113 A1—GE Healthcare] describes the preparation of a suspension of microbubbles with adjusted sizes and subsequently lyophilization with a sucrose solution thereof.

Ref4 [WO97/29782 A1—NICOMED IMAGING A/S] teaches that USCA precursors which are stable at room temperature (RT) can be prepared by lyophilization of $C_3F_8$ microbubbles in the presence of a freeze-drying stabilizer, preferably sucrose.

Up to now, according to Applicant's knowledge, such technique has not been applied yet for preparing a freeze-dried composition from a suspension of calibrated microvesicles.

As observed by the Applicant, one of the most challenging issue in preparing a freeze-dried composition of calibrated microvesicles is related to the need of avoiding substantial modification of the characteristics of the initial suspension of calibrated microvesicles, such as concentration, monodispersity or geometric standard deviation (GSD) and/or final mean diameter.

The Applicant has now found that such initial characteristics, can be preserved to an acceptable extent after the freeze-drying process by using a suitable mixture of freeze-drying protecting components.

SUMMARY OF THE INVENTION

In a first aspect, the present invention relates to a freeze-dried composition comprising an amphiphilic material and a freeze-drying protecting component which, upon reconstitution with a pharmaceutically acceptable solution in the presence of a biocompatible gas, provides a suspension of calibrated gas-filled microvesicles, wherein said freeze-drying protecting component is a mixture of at least two freeze-drying protecting components and wherein said reconstituted suspension of calibrated gas-filled microvesicles have a geometric standard deviation (GSD) lower than 1.2.

In a preferred embodiment of the invention, the mixture of freeze-drying protecting components comprises a polymer, preferably a hydrophilic polymer, more preferably a polyglycol, and a polyol or a saccharide.

In a still more preferred embodiment, said mixture comprises a polyethylene glycol (PEG) and sorbitol or PEG and sucrose.

In a preferred embodiment, said reconstituted suspension of calibrated microvesicles is characterized by a GSD of at least 1.2 or lower, preferably of at least 1.15, down to e.g. 1.1.

In an embodiment of the invention, said reconstituted suspension of calibrated microvesicles is characterized by a concentration of at least $2.0 \times 10^8$ CMV/mL, preferably $2.25 \times 10^8$ CMV/mL, more preferably $2.5 \times 10^8$ CMV/mL, up to $5.5 \times 10^8$ CMV/mL.

According to a further aspect, the invention relates to a method of preparing a freeze-dried composition for the preparation of a reconstituted suspension of calibrated gas-filled microvesicles, comprising the steps of:

a. preparing a suspension of calibrated gas-filled microvesicles comprising a mixture of freeze-drying protecting components;

b. freeze-drying the calibrated microvesicles suspension.

A further aspect of the invention relates to a freeze-dried composition for preparing a suspension of calibrated gas-filled microvesicles, said freeze-dried composition being obtainable by a process comprising the following steps:

a. preparing a first suspension of gas-filled calibrated microvesicles by a flow-focusing process, said suspension further comprising a mixture of freeze-drying protecting components:
and
b. freeze-drying said suspension.

A further aspect of the invention relates to a process for the preparation of an injectable contrast agent comprising a suspension of gas-filled microvesicles, wherein said process comprises reconstituting a freeze-dried composition as defined above, with a pharmaceutically acceptable solution in the presence of a biocompatible gas.

FIGURES

FIG. 1: Typical particles size distribution representation.

Figure 2:
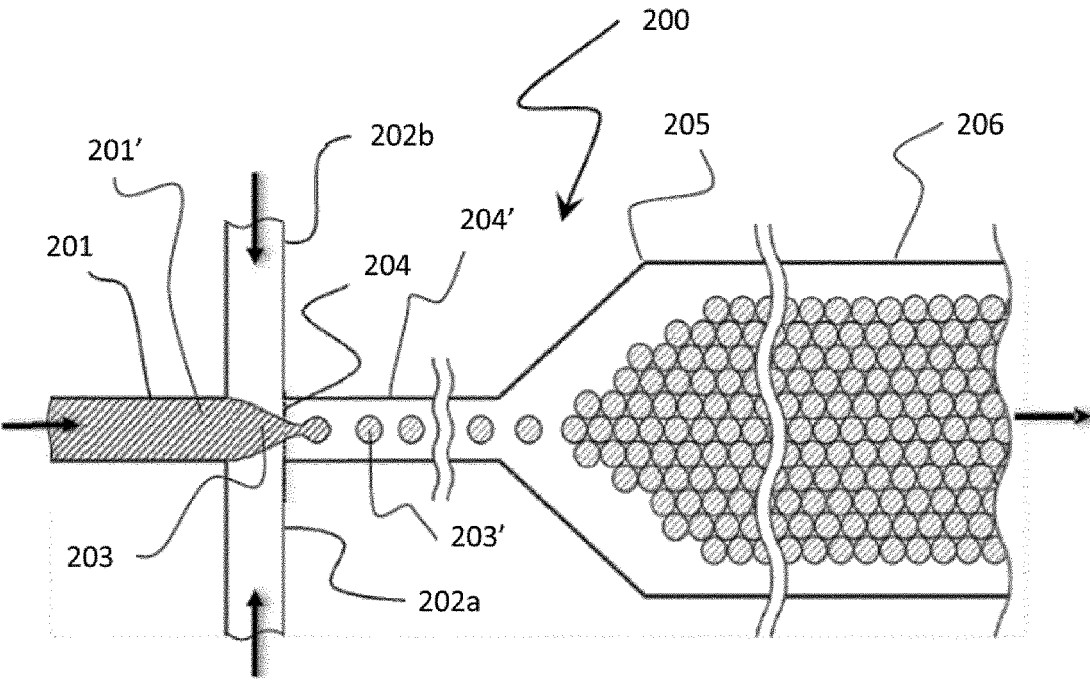

FIG. 2: Schematic representation of the core portion of a microfluidic flow-focusing device.

Figure 3:
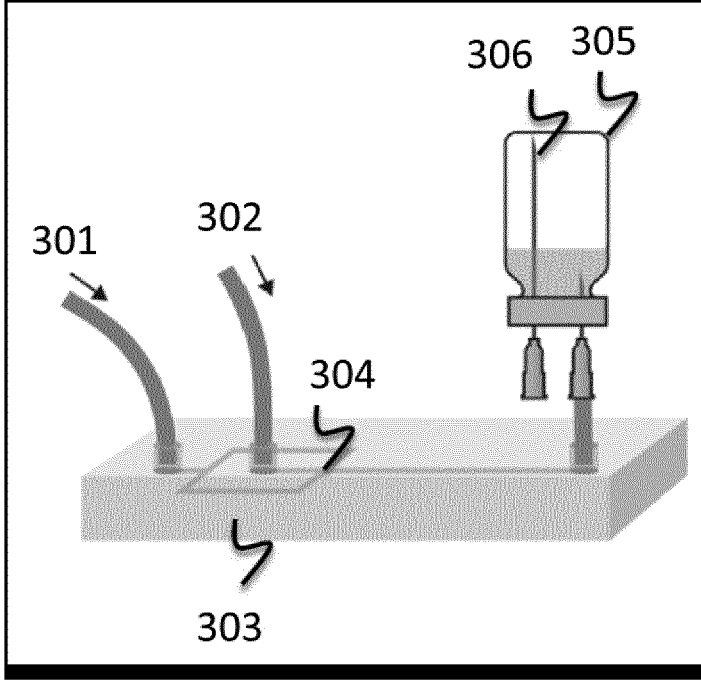

FIG. 3: An exemplary schematic drawing of a device useful for the process of the invention technology.

DETAILED DESCRIPTION OF THE INVENTION

The expression "gas-filled microvesicles" generally refers to bubbles of gas bounded, at the gas/liquid interface, by a very thin envelope (film) involving a stabilizing amphiphilic material, typically a phospholipid, disposed at the gas to liquid interface. Said calibrated gas-filled microvesicles are suitable as contrast agents in ultrasound imaging techniques, known as Contrast-Enhanced Ultrasound (CEUS) Imaging, or in therapeutic applications, e.g. in combination with ultrasound mediated drug delivery.

These stabilized gas bubbles (dispersed in a suitable physiological solution) are generally referred to in the art with various terminologies, depending typically from the stabilizing material employed for their preparation; these terms include, for instance, "microspheres", "microbubbles", "microcapsules" or "microballoons", globally referred to here as "gas-filled microvesicles" (or "microvesicles" in short).

The term "calibrated" (when referred to gas-filled microvesicles) specifically refers to microvesicles suspensions with highly calibrated microvesicles (CMV), having different sizes between 3 and 8 µm, characterized by a size distribution having a geometric standard deviation (GSD) of at least 1.2 or lower, preferably of at least 1.1, down to e.g. 1.05.

In this description and claims, the term "calibrated" is used interchangeably with "size-controlled", "monodispersed" or "monosize(d)" microvesicles.

In the present invention, calibrated gas filled microvesicles are preferably produced by using a microfluidic flow-focusing technology, where a gas thread is focused between two liquid flows in a flow-focusing device and phospholipid-stabilized calibrated microvesicles form and are collected in the outlet channel. Through this approach calibrated microvesicles are manufactured in a highly reproducible way at a reasonable production rate (~60 million bubbles per minute) (FIG. 2 and FIG. 3).

Depending on the parameters of the manufacturing process and device, the calibrated microvesicles may be obtained with relatively narrow size distribution around any desired mean diameter, e.g. from 3 to 8 µm, preferably about 4 µm.

The size distribution of said calibrated microvesicles is typically characterized by a geometric standard deviation (GSD) value of at least 1.2 or lower, preferably of at least 1.1, down to e.g. 1.05.

The calibrated microvesicles concentration (particularly upon production with microfluidic flow-focusing) is typically comprised between $3 \times 10^8$ and $4 \times 10^8$ CMV/mL, preferably close to $4 \times 10^8$ CMV/mL, not lower than $3 \times 10^8$ CMV/mL.

The "geometric standard deviation" (GSD) generally provides a suitable value for characterizing the breath of the size distribution in a population of particles (gas-filled microvesicles in the specific case). A population of particles with a broad range of sizes will thus have a larger GSD value than one in which the particles sizes are narrowly distributed around a mean value (i.e. relatively similar in size)

FIG. 1 shows an example of a size distribution graph (by volume) of a population of gas filled microvesicles which can be obtained with a commercial measuring device (e.g. Coulter Counter Multisizer 3, equipped with the Multisizer 3 software), by determining the volume of gas for each of its channels, each channel corresponding to a predetermined diameter of the microvesicles (e.g. with increments of 0.1 microns). By the determination of the number of calibrated gas-filled microvesicles in the suspension, their respective diameter and volume distribution in a selected size range (e.g. between 3 µm and 6 µm for a 4.5 µm CMV mean diameter), it is possible to calculate the GSD of a CMV distribution, by using the following Equation 1:

$$GSD = e^{\sqrt{\frac{\sum\left[n_i(lnx_i - ln\bar{x})^2\right]}{\sum n_i}}} \qquad \text{Eq. 1}$$

Where:
$n_i$=percentage of volume of gas (with respect to the total one) entrapped in the microvesicles measured for the $i^{th}$ channel
$x_i$=volume of the microvesicles in the ith channel, where $$x_i = d_i^3 \cdot \pi/6 \qquad \text{Eq. 1.1.}$$

($d_i$=diameter of the microvesicle in the $i_{th}$ channel center)
$\bar{x}$=geometric mean of the volume of the microvesicles in the selected range, where:

$$\bar{x} = 10^{\left[\frac{\sum(n_i \cdot logx_i)}{\sum n_i}\right]} \qquad \text{Eq. 1.2}$$

Among the various commercially available measuring devices, the Coulter Counter Multisizer 3, equipped with the Multisizer 3 software, is capable of calculating and providing such GSD value as defined above.

For instance, a GSD value of 1.2 indicates that about the 50% of CMV are calibrated between 2.5 and 5 µm, for a mean diameter of 4 µm; a GSD of 1.05-1.08 (<1.1) indicates that about the 90-95% of CMV have sizes comprised between 2.5 and 5 µm.

The expression "microvesicles concentration" as used herein refers to the number of CMV in a volume unit, determined using a Coulter Counter apparatus, i.e. number of CMV/mL.

As observed by the Applicant, while said calibrated microvesicles obtained through microfluidic flow-focusing can be stored at room temperature for few weeks without substantial impacts on their main characteristics, after said storage period the characteristics of said microvesicles (e.g.

concentration and size distribution) may not be maintained and may progressively deteriorate.

The shelf-life of such suspensions of gas-filled microvesicles is thus relatively short for a pharmaceutical product and there is a need to develop a long-term storage procedure, able to preserve the CMV initial characteristics, such as concentration, GSD and final diameter for longer times, e.g. months or years.

The lyophilization process is a suitable approach to obtain a calibrated microvesicles dry form, with increased stability over time and with preserved initial characteristics.

It has now been surprisingly found that CMV initial characteristics, such as concentration, GSD and final diameter, can be substantially preserved after the freeze-drying process by using suitable combinations of freeze-drying protecting components, as compared to a freeze-drying process using the same freeze-drying protecting components as single additive.

In a first aspect, the present invention provides a freeze-dried composition comprising an amphiphilic material and a mixture of freeze-drying protecting components, which upon reconstitution with a suitable aqueous solution in the presence of biocompatible gas, provides a suspension of calibrated gas-filled microvesicles, wherein said microvesicles have a GSD value of at least 1.2 or lower, preferably of at least 1.15, down to e.g. 1.1.

In the present description and claims, the term "freeze-drying" and "lyophilization" are used interchangeably, as well the terms "freeze-dried" and "lyophilized".

Freeze-Dried Composition

As used herein, the expression "freeze-dried composition" indicates any dry dosage form for long-term storage of gas-filled microvesicles formulations obtained through a lyophilization process. Said freeze-dried composition can comprise one or more active ingredient and a mixture of at least two freeze-drying protecting components.

The expression "active ingredient" as used herein indicates the microvesicle-stabilizing materials, e.g. the amphiphilic materials, which are comprised in the freeze-dried composition with the freeze-drying protecting components.

Mixture of Freeze-Drying Protecting Components

As used herein, the expression "mixture of freeze-drying protecting components" refers to a combination of at least two components suitable for freeze drying, which is included in the microvesicles suspension before the lyophilization process thereof.

The term "freeze-drying protecting components" designates any compound added to protect the active ingredient during any phase of the freeze-drying process. Examples of suitable freeze-drying protecting components are polyethylene glycols (PEG), polyols, saccharides, surfactants, buffers, amino acids, chelating complexes, and inorganic salts.

According to an embodiment of the invention, said mixture of freeze-drying protecting components is a combination of at least two different compounds suitable for freeze-drying, selected among the group of polymers, polyols and saccharides. Preferably said mixture comprises a combination of a polymer with a polyol or a saccharide.

In a preferred embodiment of the invention one of the components of the mixture of freeze-drying protecting components is a polymer, preferably a hydrophilic polymer, more preferably a polyglycol.

In a still more preferred embodiment, said polyglycol is a polyethylene glycol (PEG). Polyethylene glycol (PEG) has its standard chemical meaning. The chemical formula of PEG is $HOCH_2(CH_2OCH_2)_mCH_2OH$ where m represents the average number of oxyethylene groups. Typical polyethylene glycols are available in a wide range of average molecular weights, starting from 190-210 g/mol (PEG 200; m=4.2) to 7000-9000 g/mol (PEG 8000; m=181.4).

According to this description, the expression "molecular weight" indicates the average length of the PEG polymer chains, with a variability of ±10% on the indicated molecular weight.

According to an embodiment of this invention, the mixture of freeze-drying protecting components preferably comprises a PEG having a molecular weight comprised between 2000 and 10000 g/mol, preferably between 4000 and 8000 g/mol.

According to an embodiment, the freeze-drying protecting component is PEG having a molecular weight of 8000 g/mol (±10%). According to another embodiment, the freeze-drying protecting component is PEG having a molecular weight close to 4000 g/mol (±10%).

In an embodiment of the invention, the mixture of freeze-drying protecting components is added to the suspension of CMV as a solution having a concentration comprised between 100 mg/mL and 300 mg/mL, preferably 120 mg/mL and 250 mg/mL, more preferred close to 200 mg/mL.

As observed by the Applicant, polymers (in particular polyglycol, e.g. PEG) suspensions with a concentration of 150 mg/mL or higher (e.g. 200 mg/mL), due to their relatively high viscosity, may be difficult to handle during industrial processes. It is thus preferable to keep using polymer suspensions with a concentration lower than 150 mg/mL.

To improve the preservation of initial characteristics of the CMV suspension reconstituted after the freeze-drying process, the Applicant has found that it is preferred using a suitable mixture of PEG at a concentration lower than 150 mg/mL (e.g. 100 mg/mL) in combination with a second freeze-drying protecting component.

In a preferred embodiment of this invention, the freeze-dried composition comprises a mixture of freeze-drying protecting components which is the combination of a polymer, preferably a polyglycol, with a polyol.

In this description and claims, the term "polyol" has its conventional chemical meaning; it indicates any organic compound with more than two hydroxyl functional groups, characterized by the general formula $HOCH_2(CHOH)_nCH_2OH$, where n is an integer from 1 to 6, preferably from 2 to 4. Polyols differ in chain length, i.e. four-, five- or six-carbon chains. They have one hydroxyl group attached to each carbon. Polyols can be further differentiated by the relative orientation (stereochemistry) of these hydroxyl groups. Suitable polyols include erythritol, xylitol, sorbitol, lactitol and mannitol.

In this invention, said polyol is preferably selected from the group of polyols having a carbon chain length from four to six carbons atoms.

In a still more preferred embodiment, said polyol is sorbitol or xylitol.

The term "sorbitol" has its conventional meaning in the chemical field. Sorbitol, or (2R,3R,4R,5S)-hexane-1,2,3,4,5,6-hexol, is a polyhydric alcohol, consisting in a linear carbon chain, with 6 carbon atoms, each one is substituted with a hydroxyl functional group. It has a molecular weight of 182.172 g/mol. Sorbitol occurs naturally and is also produced synthetically from glucose. It is isomeric with mannitol.

The term "xylitol" has its conventional meaning in the chemical field. Xylitol, or (2S,4R)-pentane-1,2,3,4,5-pentol, is a five-carbon sugar alcohol, where all five carbon atoms of the molecule bind a hydroxyl group. Its molecular weight is 152.146 g/mol.

In a still further embodiment, the freeze-dried composition comprises a mixture of a polymer with a saccharide.

The term "saccharide" has its standard meaning in the field of chemistry. Saccharides, also called carbohydrates, are molecular compounds made from just three elements: carbon, hydrogen and oxygen. The simplest saccharides are called monosaccharides and they are the building units for bigger saccharides, such as disaccharides, trisaccharide and polysaccharides.

Preferably, said saccharide is selected from the group of disaccharides, trisaccharides and polysaccharides, more preferably a disaccharide or trisaccharide.

Monosaccharides have the general molecular formula $(CH_2O)_n$, where n can be 3, 5 or 6. Monosaccharides can form cyclic structures by the reaction of the carbonyl group with an OH group. These cyclic molecules can in turn react with another alcohol. Suitable examples of monosaccharides include glucose, fructose and galactose.

Disaccharides $(C_{12}H_{22}O_{11})$ are sugars composed of two monosaccharide units that are joined by a glycosidic bond. This latter is a covalent bond formed from the reaction of the anomeric carbon of one cyclic monosaccharide with the OH group of a second monosaccharide. Disaccharides differ from one another in their monosaccharide constituents and in the specific type of glycosidic linkage connecting them. Examples of disaccharides include: maltose, lactose, and sucrose. Particularly preferred among the disaccharides is sucrose.

Trisaccharides are saccharides composed of three monosaccharides with two glycosidic bonds connecting them. Similar to the disaccharides, each glycosidic bond can be formed between any hydroxyl group on the component monosaccharides. Even if all three component sugars are the same (e.g., glucose), different bond combinations (regiochemistry) and stereochemistry (alpha- or beta-) result in trisaccharides that are diastereoisomers with different chemical and physical properties. Examples of trisaccharides are maltotriose, melezitose, maltotriose and raffinose. Particularly preferred among the trisaccharides is raffinose.

Polysaccharides are polymeric saccharide molecules composed of long chains of monosaccharide units bound together by glycosidic linkages. They range in structure from linear to highly branched. Examples of polysaccharides are: starch, cellulose, dextran and chitin. Particularly preferred among the polysaccharides is dextran.

In a preferred embodiment of this invention said saccharide is a disaccharide, more preferably sucrose.

In this invention the term "sucrose" is its standard meaning. Sucrose is a disaccharide formed by glucose and fructose units linked by an acetal oxygen bridge from hemiacetal of glucose to the hemiketal of the fructose. Sucrose has an empirical formula of $C_{12}H_{22}O_{11}$ and a molecular weight of 342.30 g/mol.

Initial CMV characteristics are particularly preserved when using a mixture of freeze-drying protecting components characterized in that said mixture of freeze-drying protecting component has a total concentration comprised between 100 mg/mL and 300 mg/mL, preferably between 120 mg/mL and 250 mg/mL, more preferably the total concentration of PEG and polyol or PEG and saccharide is 200 mg/mL.

In a preferred embodiment, the mixture of freeze-drying protecting components comprises a PEG and a polyol or a PEG and a saccharide in a ratio between 2:1 to 2:3, preferably between 3:2 to 4:5, more preferably 1:1.

The above mixtures of freeze-drying protecting components have shown advantageous results when used in the freeze-drying process of the calibrated microvesicles suspensions, to prepare a freeze-dried composition which can then be reconstituted to obtain suspensions of calibrated microvesicles having acceptable characteristics in terms of concentration and size distribution.

Amphiphilic Material

Materials suitable for forming the stabilizing layer of the gas-filled microvesicle (i.e. microvesicle-stabilizing materials) are those known in the art. These preferably include amphiphilic materials.

The term "amphiphilic material" as used herein includes compounds having a molecule with a hydrophilic polar head portion (e. g. a polar or ionic group), capable of interacting with an aqueous medium, and a hydrophobic organic tail portion (e. g. a hydrocarbon chain), capable of interacting with e. g. an organic solvent. These compounds thus generally act as "surface active agent", i.e. compounds which are capable of stabilizing mixtures of otherwise generally immiscible materials, such as mixtures of two immiscible liquids (e. g. water and oil), mixtures of liquids with gases (e. g. gas microbubbles in water) or mixtures of liquids with insoluble particles (e.g. metal nanoparticles in water).

Suitable amphiphilic materials comprise, for instance, phospholipids; lysophospholipids; fatty acids, such as palmitic acid, stearic acid, arachidonic acid or oleic acid; lipids bearing polymers, such as chitin, hyaluronic acid, polyvinylpyrrolidone or polyethylene glycol (PEG), also referred as "pegylated lipids"; lipids bearing sulfonated mono- di-, oligo- or polysaccharides; cholesterol, cholesterol sulfate or cholesterol hemisuccinate; tocopherol hemisuccinate; lipids with ether or ester-linked fatty acids; polymerized lipids; diacetyl phosphate; dicetyl phosphate; ceramides; polyoxyethylene fatty acid esters (such as polyoxyethylene fatty acid stearates), polyoxyethylene fatty alcohols, polyoxyethylene fatty alcohol ethers, polyoxyethylated sorbitan fatty acid esters, glycerol polyethylene glycol ricinoleate, ethoxylated soybean sterols, ethoxylated castor oil or ethylene oxide (EO) and propylene oxide (PO) block copolymers; sterol esters of sugar acids including cholesterol glucuronides, lanosterol glucuronides, 7-dehydrocholesterol glucuronide, ergosterol glucuronide, cholesterol gluconate, lanosterol gluconate, or ergosterol gluconate; esters of sugar acids and alcohols including lauryl glucuronide, stearoyl glucuronide, myristoyl glucuronide, lauryl gluconate, myristoyl gluconate, or stearoyl gluconate; esters of sugars with aliphatic acids including sucrose laurate, fructose laurate, sucrose palmitate, sucrose stearate, glucuronic acid, gluconic acid or polyuronic acid; saponins including sarsasapogenin, smilagenin, hederagenin, oleanolic acid, or digitoxigenin; glycerol or glycerol monoesters with fatty acids, including glycerol monopalmitate, glycerol monostearate, glycerol monomyristate or glycerol monolaurate; long chain alcohols including n-decyl alcohol, lauryl alcohol, myristyl alcohol, cetyl alcohol, or n-octadecyl alcohol; 6-(5-cholesten-3β-yloxy)-1-thio-β-D-galactopyranoside; digalactosyldiglyceride; 6-(5-cholesten-3 β-yloxy)hexyl-6-amino-6-deoxy-1-thio-β-D-galactopyranoside; 6-(5-cholesten-3 β-yloxy) hexyl-6-amino-6-deoxyl-1-thio-β-D-mannopyranoside; 12-(((7'-diethylaminocoumarin-3-yl)carbonyl)-methylamino) octadecanoic acid; N-[12-(((7'-diethylaminocoumarin-3-yl) carbonyl)-methylamino)octadecanoyl]-2-aminopalmitic acid; N-succinyldioleylphosphatidylethanol-amine; 1,2-dioleyl-sn-glycerol; 1,2-dipalmitoyl-sn-3-succinylglycerol;

1,3-dipalmitoyl-2-succinylglycerol; 1-hexadecyl-2-palmitoylglycerophosphoethanolamine or palmitoyl-homocysteine; alkylamines or alkylammonium salts, comprising at least one ($C_{10}$-$C_{20}$), preferably ($C_{14}$-$C_{18}$), alkyl chain, such as, for instance, N-stearylamine, N,N'-distearylamine, N-hexadecylamine, N,N'-dihexadecylamine, N-stearylammonium chloride, N,N'-distearylammonium chloride, N-hexadecylammonium chloride, N,N'-dihexadecylammonium chloride, dimethyldioctadecylammonium bromide (DDAB), hexadecyltrimethylammonium bromide (CTAB); tertiary or quaternary ammonium salts comprising one or preferably two ($C_{10}$-$C_{20}$), preferably ($C_{14}$-$C_{18}$), acyl chain linked to the N-atom through a ($C_3$-$C_6$) alkylene bridge, such as, for instance, 1,2-distearoyl-3-trimethylammonium-propane (DSTAP), 1,2-dipalmitoyl-3-trimethylammonium-propane (DPTAP), 1,2-oleoyl-3-trimethylammonium-propane (DOTAP), 1,2-distearoyl-3-dimethylammonium-propane (DSDAP); and mixtures or combinations thereof.

According to this invention, the amphiphilic material is preferably a phospholipid.

The term "phospholipid" is intended to encompass any amphiphilic phospholipidic compound, the molecules of which are capable of forming a stabilizing film of material (typically in the form of a mono-molecular layer) at the gas-water boundary interface in the final microbubbles suspension. Accordingly, these materials are also referred to in the art as "film-forming phospholipids".

Examples of suitable phospholipids include esters of glycerol with one or preferably two (equal or different) residues of fatty acids and with phosphoric acid, wherein the phosphoric acid residue is in turn bound to a hydrophilic group, such as, for instance, choline (phosphatidylcholines—PC), serine (phosphatidylserines—PS), glycerol (phosphatidylglycerols—PG), ethanolamine (phosphatidylethanolamines—PE), inositol (phosphatidylinositol). Esters of phospholipids with only one residue of fatty acid are generally referred to in the art as the "lyso" forms of the phospholipid or "lysophospholipids". Fatty acids residues present in the phospholipids are in general long chain aliphatic acids, typically containing from 12 to 24 carbon atoms, preferably from 14 to 22; the aliphatic chain may contain one or more unsaturations or is preferably completely saturated. Examples of suitable fatty acids included in the phospholipids are, for instance, lauric acid, myristic acid, palmitic acid, stearic acid, arachidic acid, behenic acid, oleic acid, linoleic acid, and linolenic acid. Preferably, saturated fatty acids such as myristic acid, palmitic acid, stearic acid and arachidic acid are employed.

Further examples of phospholipids are phosphatidic acids, i.e. the diesters of glycerol-phosphoric acid with fatty acids; sphingolipids such as sphingomyelins, i.e. those phosphatidylcholine analogs where the residue of glycerol diester with fatty acids is replaced by a ceramide chain; cardiolipins, i.e. the esters of 1,3-diphosphatidylglycerol with a fatty acid; glycolipids such as gangliosides GM1 (or GM2) or cerebrosides; glucolipids; sulfatides and glycosphingolipids.

As used herein, the term "phospholipids" include either naturally occurring, semisynthetic or synthetically prepared products that can be employed either singularly or as mixtures.

Examples of naturally occurring phospholipids are natural lecithins (phosphatidylcholine (PC) derivatives) such as, typically, soya bean or egg yolk lecithins.

Examples of semisynthetic phospholipids are the partially or fully hydrogenated derivatives of the naturally occurring lecithins. Preferred phospholipids are fatty acids diesters of phosphatidylcholine, ethylphosphatidylcholine, phosphatidylglycerol, phosphatidic acid, phosphatidylethanolamine, phosphatidylserine, phosphatidylinositol or of sphingomyelin.

Examples of preferred phospholipids are, for instance, dilauroyl-phosphatidylcholine (DLPC), dimyristoyl-phosphatidylcholine (DMPC), dipalmitoyl-phosphatidylcholine (DPPC), diarachidoyl-phosphatidylcholine (DAPC), distearoyl-phosphatidylcholine (DSPC), dioleoyl-phosphatidylcholine (DOPC), 1,2 Distearoyl-sn-glycero-3-Ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-stearoyl-phosphatidylcholine (PSPC), 1-stearoyl-2-palmitoyl-phosphatidylcholine (SPPC), 1-palmitoyl-2-oleylphosphatidylcholine (POPC), 1-oleyl-2-palmitoyl-phosphatidylcholine (OPPC), dilauroyl-phosphatidylglycerol (DLPG) and its alkali metal salts, diarachidoylphosphatidyl-glycerol (DAPG) and its alkali metal salts, dimyristoylphosphatidylglycerol (DMPG) and its alkali metal salts, dipalmitoylphosphatidylglycerol (DPPG) and its alkali metal salts, distearoylphosphatidylglycerol (DSPG) and its alkali metal salts, dioleoyl-phosphatidylglycerol (DOPG) and its alkali metal salts, dimyristoyl phosphatidic acid (DMPA) and its alkali metal salts, dipalmitoyl phosphatidic acid (DPPA) and its alkali metal salts, distearoyl phosphatidic acid (DSPA), diarachidoylphosphatidic acid (DAPA) and its alkali metal salts, dimyristoyl-phosphatidylethanolamine (DMPE), dipalmitoylphosphatidylethanolamine (DPPE), distearoyl phosphatidyl-ethanolamine (DSPE), dioleylphosphatidyl-ethanolamine (DOPE), diarachidoylphosphatidylethanolamine (DAPE), dilinoleylphosphatidylethanolamine (DLPE), dimyristoyl phosphatidylserine (DMPS), diarachidoyl phosphatidylserine (DAPS), dipalmitoyl phosphatidylserine (DPPS), distearoylphosphatidylserine (DSPS), dioleoylphosphatidylserine (DOPS), dipalmitoyl sphingomyelin (DPSP), and distearoylsphingomyelin (DSSP), dilauroyl-phosphatidylinositol (DLPI), diarachidoylphosphatidylinositol (DAPI), dimyristoylphosphatidylinositol (DMPI), dipalmitoylphosphatidylinositol (DPPI), distearoylphosphatidylinositol (DSPI), dioleoyl-phosphatidylinositol (DOPI).

Suitable phospholipids further include phospholipids modified by linking a hydrophilic polymer, such as polyethyleneglycol (PEG) or polypropyleneglycol (PPG), thereto. Preferred polymer-modified phospholipids include "pegylated phospholipids", i.e. phospholipids bound to a PEG polymer. Examples of pegylated phospholipids are pegylated phosphatidylethanolamines ("PE-PEGs" in brief) i.e. phosphatidylethanolamines where the hydrophilic ethanolamine moiety is linked to a PEG molecule of variable molecular weight (e.g. from 300 to 20000 daltons, preferably from 500 to 5000 daltons), such as DPPE-PEG (or DSPE-PEG, DMPE-PEG, DAPE-PEG or DOPE-PEG). For example, DPPE-PEG2000 refers to DPPE having attached thereto a PEG polymer having a mean average molecular weight of about 2000.

Particularly preferred phospholipids are DAPC, DSPC, DPPC, DMPA, DPPA, DSPA, DMPG, DPPG, DSPG, DMPS, DPPS, DSPS and Ethyl-DSPC. Most preferred are DPPG, DPPS and DSPC.

Mixtures of phospholipids can also be used, such as, for instance, mixtures of DPPE and/or DSPE (including pegylated derivatives), DPPC, DSPC and/or DAPC with DSPS, DPPS, DSPA, DPPA, DSPG, DPPG, Ethyl-DSPC and/or Ethyl-DPPC.

For instance, a mixture of phospholipids may include phosphatidylcholine derivatives, phosphatidic acid derivatives and pegylated phosphatidylethanolamine, e.g. DSPC/DPPA/DPPE-PEG, DPPC/DPPA/DPPE-PEG, DSPC/DPPA/DSPE-PEG, DPPC/DPPA/DSPE-PEG, DAPC/DPPA/DPPE-PEG, DAPC/DPPA/DSPE-PEG, DSPC/DSPA/DPPE-PEG, DPPC/DSPA/DSPE-PEG, DSPC/DSPG/DPPE-PEG, DPPC/DSPG/DSPE-PEG.

According to the present invention, the phospholipid can conveniently be used in admixtures with any of the above listed amphiphilic compounds. Thus, for instance, lipids such as cholesterol, ergosterol, phytosterol, sitosterol, lanosterol, tocopherol, propyl gallate or ascorbyl palmitate, fatty acids such as myristic acid, palmitic acid, stearic acid, arachidic acid and derivatives thereof or butylated hydroxytoluene and/or other non-phospholipid compounds can optionally be added to one or more of the foregoing phospholipids, e.g in proportions preferably ranging from zero to 50% by weight, more preferably up to 25%. For instance, mixtures of amphiphilic materials comprising phospholipids and fatty acids can advantageously be used, including DSPC/DPPG/palmitic acid, DSPC/DPPE-PEG/palmitic acid, DPPC/DPPE-PEG/palmitic acid, DSPC/DSPE-PEG/palmitic acid, DPPC/DSPE-PEG/palmitic acid, DSPC/DPPE-PEG/stearic acid, DPPC/DPPE-PEG/stearic acid, DSPC/DSPE-PEG/stearic acid or DPPC/DSPE-PEG/stearic acid.

The microvesicles prepared according to the invention may optionally comprise a targeting ligand.

The term "targeting ligand" includes within its meaning any compound, moiety or residue having, or being capable to promote, a targeting activity (e.g. including a selective binding) of the microvesicles of a composition of the invention towards any biological or pathological site within a living body. Targets with which targeting ligand may be associated include tissues such as, for instance, myocardial tissue (including myocardial cells and cardiomyocytes), membranous tissues (including endothelium and epithelium), laminae, connective tissue (including interstitial tissue) or tumors; blood clots; and receptors such as, for instance, cell-surface receptors for peptide hormones, neurotransmitters, antigens, complement fragments, and immunoglobulins and cytoplasmic receptors for steroid hormones.

The targeting ligand may be synthetic, semi-synthetic, or naturally occurring. Materials or substances which may serve as targeting ligands include, for example, but are not limited to proteins, including antibodies, antibody fragments, receptor molecules, receptor binding molecules, glycoproteins and lectins; peptides, including oligopeptides and polypeptides; peptidomimetics; saccharides, including mono and polysaccharides;

vitamins; steroids, steroid analogs, hormones, cofactors, bioactive agents and genetic material, including nucleosides, nucleotides and polynucleotides.

The targeting ligand may be an amphiphilic compound per se (which is admixed with the other components of the microvesicle) or a compound bound to an amphiphilic molecule (e.g. a phospholipid) employed for the formation of the microvesicles.

Gas

Suitable gases comprise biocompatible fluorinated gases, preferably perfluorinated gases. Fluorinated gases include materials which contain at least one fluorine atom such as, for instance, fluorinated hydrocarbons (organic compounds containing one or more carbon atoms and fluorine); sulfur hexafluoride; fluorinated, preferably perfluorinated, ketones such as perfluoroacetone; and fluorinated, preferably perfluorinated, ethers such as perfluorodiethyl ether. Preferred compounds are perfluorinated gases, such as $SF_6$ or perfluorocarbons (perfluorinated hydrocarbons), i.e. hydrocarbons where all the hydrogen atoms are replaced by fluorine atoms, which are known to form particularly stable gas-filled microvesicles suspensions.

The term "perfluorocarbon" includes saturated, unsaturated, and cyclic perfluorocarbons. Examples of biocompatible, physiologically acceptable perfluorocarbons are: perfluoroalkanes, such as perfluoromethane, perfluoroethane, perfluoropropanes, perfluorobutenes (e.g. perfluoro-n-butane, optionally in admixture with other isomers such as perfluoro-isobutane), perfluoropentanes, perfluorohexanes or perfluoroheptanes; perfluoroalkenes, such as perfluoropropene, perfluorobutenes (e.g. perfluorobut-2ene) or perfluorobutadiene; perfluoroalkynes (e.g. perfluorobut-2-yne); and perfluorocycloalkanes (e.g. perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane). Preferred saturated perfluorocarbons include, for example, $CF_4$, $C_2F_6$, $C_3F_8$, $C_4F_8$, $C_4F_{18}$, $C_5F_{12}$ and $C_6F_{14}$ Particularly preferred gases are those which are in gaseous form at room temperature, including $SF_6$, $C_3F_8$, and $C_4F_{10}$.

An aspect of this invention thus relates to a method of preparing a freeze-dried composition for long term storage of calibrated gas-filled microvesicles, comprising the steps of:

a. preparing a suspension of calibrated gas-filled microvesicles comprising a mixture of freeze-drying protecting components;

b. freeze-drying the calibrated microvesicles suspension.

Preferably, the method of preparation of step a) is the microfluidic flow-focusing technique, as illustrated in Ref.1 [WO2018/041906 A1—BRACCO SUISSE SA] and Ref.2 [PCT application number PCT/EP2019/055325].

FIG. 2 shows a schematic representation of the core portion 200 of a flow-focusing device ("microfluidic chip") useful in the process of the invention. The chip comprises a first feed channel 201 for feeding the gaseous flow 201' and two additional orthogonal feed channels 202a and 202b for supplying the liquid flow comprising the amphiphilic material.

The gas flow and the two liquid flows are directed towards the contact zone 203 and then through the calibrated orifice 204, shown as a dotted line in FIG. 1. The calibrated orifice is connected to a calibrated channel 204' having preferably the same cross-section as the orifice, which is in turn connected to an initial portion 205 of the outlet channel 206. In an alternative embodiment (not shown) the calibrated orifice 204 may be a nozzle directly connected to the initial portion 205 of outlet channel 206 i.e. without the calibrated channel in-between. The microvesicles 203' are formed in the calibrated orifice and directed, through calibrated channel 204', to the initial portion 205 of the outlet channel 206. The hydraulic diameter of the outlet channel is generally larger than the hydraulic diameter of the calibrated orifice and typically increases from the initial diameter of the calibrated orifice to the final diameter of the outlet channel 206, corresponding substantially to the hydraulic diameter of a collecting tube (not shown), connecting the flow-focusing device to a container, e.g. a sealed vial for collecting the suspension of microvesicles.

In the initial portion 205 of the outlet channel of the device and preferably also in the contact zone 203 and in the calibrated orifice 204 the temperature of the microvesicles is controlled, as described in Ref.1 [WO2018/041906 A1—BRACCO SUISSE SA] and Ref.2 [PCT application number PCT/EP2019/055325].

Liquid Flow

The aqueous liquid flow for preparing the calibrated gas-filled microvesicles according to the method of the invention comprises an amphiphilic material (as above defined) at a concentration of e.g. from 5.0 to 20 mg/mL, preferably from 7.5 to 15 mg/mL, dispersed in an aqueous carrier.

Suitable aqueous carriers, which are preferably physiologically acceptable, comprise water (preferably sterile water), aqueous solutions such as saline (which may advantageously be balanced so that the final product for injection is not hypotonic), or solutions of one or more tonicity adjusting substances. Tonicity adjusting substances comprise salts or sugars, sugar alcohols, glycols or other non-ionic polyol materials (e.g. glucose, sucrose, sorbitol, mannitol, glycerol, polyethylene glycols, propylene glycols and the like), chitosan derivatives, such as carboxymethyl chitosan, trimethyl chitosan or gelifying compounds, such as carboxymethylcellulose, hydroxyethyl starch or dextran.

In an alternative embodiment, an additional oil phase may be added for incorporating therapeutic hydrophobic substances into the microvesicles. To this end, two additional conduits may be provided in the device for supplying the desired oil phase, as described for instance by Ref.1 [WO2018/041906 A1—BRACCO SUISSE SA] and Ref.2 [PCT application number PCT/EP2019/055325]. The formed gas-filled microvesicles will thus have a film of oil disposed at the interface between gas and the stabilizing layer of amphiphilic material, which can be loaded with a desired therapeutic agent. Suitable oils may include any biocompatible oil which is liquid at room temperature including, for instance, mono-, di- or tri-esters of glycerol with saturated or unsaturated ($C_2$-$C_{18}$) alkyl chains (including homo- or hetero-allkylesters), such as glycerol monobutyrin, glycerol monolinoleate, 1,2-dihexanoyl glycerol, 1,2 dioctanoyl glycerol, 1,2-dioleyl-sn-glycerol, triacetin, tributyrin, tricaproin, tricaprylin, tricaprin, and mixtures thereof; or natural oils such as soya oil, olive oil, safflower seed oil, sunflower seed oil, peanut oil and mixtures thereof.

Mixed Gas Flow

The freshly formed microvesicles comprise a gas selected among those previously indicated. Preferably the gas is a mixture of a gas highly soluble in water ("HS gas") and of a gas with low solubility in water ("LS gas"), as anticipated in Ref. 2 [PCT application number PCT/EP2019/055325].

During the stabilization phase, the major amount of the highly soluble gas rapidly dissolves in water while the poorly soluble one remains entrapped into the densely packed layer of amphiphilic compounds, typically with some residual amount of HS solubility gas dispersed therein.

Examples of HS gases include nitrogen, air, and carbon dioxide, this latter being particularly preferred because of its higher solubility in water.

Suitable LS gases are fluorinated gases, preferably perfluorinated gases. Fluorinated gases those previously described in the present description.

In a preferred embodiment of the invention, gas-filled microvesicles comprising $CO_2$/$C_4F_{10}$ in a volume ratio of from 80/20 to 90/10, e.g. 85/15, can be prepared with a gas-mixing device similar to the one schematically illustrated in FIG. 3.

FIG. 3 shows an example of a microfluidic flow-focusing device used for the production of calibrated microvesicles.

A gas flow 302 (comprising e.g. a mixture of $C_4F_{10}$ and $CO_2$) and a liquid flow 301 (comprising an amphiphilic material, e.g. a phospholipid, fatty acid or mixtures thereof), are supplied to microfluidic chip 303 to produce microvesicles through orifice 304. The microvesicles suspension is collected in a vial 305, which is preferably prefilled with a gas (e.g. $C_4F_{10}$) at ambient pressure. A venting device (e.g. a needle 306) is preferably used to equalize the overpressure generated by the liquid filling of the vial. At the end of the collection of the microvesicles suspension, the venting device is preferably removed and the container is preferably sealed to avoid further gaseous exchange with the external atmosphere.

According to a preferred embodiment of this invention, after the collection phase, the calibrated microvesicles obtained through the microfluidic flow-focusing method, are treated using suitable washing techniques, in order to remove not-assembled amphiphilic material and possible residue compounds.

In the present description, the term "washing" indicates any operation carried out on the freshly prepared microvesicles suspension, finalized to remove (or substantially reduce the amount of) not-assembled amphiphilic material and residue compounds.

According to this description, suitable washing techniques comprise centrifugation, filtration, bubble sorting and decantation.

In the present description, the expression "not-assembled amphiphilic material" indicates amphiphilic molecules that, at the end of the preparation process, are present in the calibrated microvesicles suspension, but are not forming the stabilizing layer of the gas-filled microvesicles.

In the present description "residues compounds" indicate any possible additive substance that is added to the amphiphilic material solution during the microvesicles preparation, such as tonicity adjusters as described before.

In a preferred embodiment of this invention, after the washing operation, a mixture of freeze-drying protecting components is added to the calibrated microvesicles suspension.

Alternatively, the mixture of freeze-drying protecting components can be added to the liquid flow comprising the amphiphilic compounds, described above, during the preparation of the microvesicles by microfluidic technique.

Initial CMV characteristics are particularly preserved when using a mixture of freeze-drying protecting components characterized in that said mixture of freeze-drying protecting component has a total concentration comprised between 100 mg/ml and 300 mg/mL, preferably between 120 mg/ml and 250 mg/mL, more preferably the total concentration of PEG and polyol or PEG and saccharide is 200 mg/mL.

In a preferred embodiment of the invention, before the freeze-drying process, the CMV suspension comprises a mixture of freeze-drying protecting components at a concentration between 10 and 25%, preferably between 14 and 24% and still more preferred between 18-22% (w/v %).

The mixture of freeze-drying protecting components represents the larger amount of the final freeze-dried preparation, wherein it is typically at least 90%, preferably between 94% and 99.7%, more preferably 99.5%, up to 99.9% (w/w).

Said mixtures of freeze-drying protecting components are those described above in the present description. Said mixture has shown advantageous results when used in the freeze-drying process of the calibrated microvesicles suspensions, to prepare a freeze-dried composition which can then be reconstituted to obtain suspensions of calibrated microvesicles having acceptable characteristics in terms of concentration and size distribution, as compared to those of the initial suspension (before freeze-drying).

For instance, using a mixture of freeze-drying protecting components results to be the best strategy to substantially preserve the GSD value after the freeze-drying process. According to an embodiment, GSD values comprised between 1.16 and 1.18 can be obtained when using a mixture of freeze-drying protecting components, in comparison with the use of a single additive which gives calibrated microvesicles characterized by a higher GSD value.

In a preferred embodiment, the use of a mixture of freeze-drying protecting components is able to significantly improve the yield of calibrated microvesicles after freeze-drying with an increase of 38%, when compared with the use of a single freeze-drying protecting component.

In this description and claims, the term freeze-drying has its standard meaning in the pharmaceutical technology field. Freeze-drying process consists of drying a pre-frozen liquid product under low pressure or vacuum and at low temperature. The main objective is to remove liquid from the product in order to provide a freeze-dried product suitable for long term storage.

As observed by the Applicant, freeze-drying parameters may be selected to further optimize the characteristics of the reconstituted suspension of microvesicles (e.g. yield, size, GSD).

In a preferred embodiment of the invention, the freezing temperature of said method for long term storage of calibrated gas-filled microvesicles, ranges between –30° C. and –70° C., preferably between –30° C. and –60° C., still more preferably –40° C.

In a still preferred embodiment, the pressure of the freeze-drying is preferably 0.5 mbar or lower, preferably 0.2 or lower, e.g. close to 0.1 mbar.

A further aspect of the invention relates to a freeze-dried composition for preparing a suspension of calibrated gas-filled microvesicles, said freeze-dried composition being obtainable by a process comprising the following steps:

a. preparing a first suspension of gas-filled calibrated microvesicles by a flow-focusing process comprising the steps of:

wherein said suspension further comprises a mixture of freeze-drying protecting components; and b. freeze-drying said suspension.

A further aspect of the invention relates to a process for the preparation of an injectable contrast agent comprising a suspension of gas-filled microvesicles, wherein said process comprises reconstituting a freeze-dried composition, obtained as described above, comprising an amphiphilic material and a mixture of freeze-drying protecting components, with a pharmaceutically acceptable solution in the presence of biocompatible gas.

The freeze-dried composition can then be reconstituted with a suitable pharmaceutically acceptable (aqueous) solution in the presence of biocompatible gas, thus providing a suspension of calibrated gas-filled microvesicles, wherein said microvesicles have a GSD of at least 1.2 or lower, preferably of at least 1.15, down to e.g. 1.1.

In this invention, pharmaceutically acceptable (aqueous) solutions are water, typically sterile, pyrogen free water (to prevent as much as possible contamination in the final reconstituted product), aqueous solutions such as saline (which may advantageously be balanced so that the final product for injection is not hypotonic), or aqueous solutions of one or more tonicity adjusting substances such as salts or sugars, sugar alcohols, glycols or other non-ionic polyol materials.

The freeze-dried composition is typically reconstituted with a volume of aqueous solution similar to the volume of suspension which underwent the freeze-drying process. Accordingly, the concentration of the freeze-drying protecting components in the reconstituted suspension is substantially the same as the one in the initial suspension. For this reason, an excessive amount of polymer (typically polyglycol, e.g. PEG), e.g. higher than 150 mg/mL (e.g. 200 mg/mL) shall preferably be avoided, in order to avoid an excessive viscosity of the suspension to be administered.

Surprisingly, the reconstituted suspensions of calibrated microvesicles were found to have substantially maintained the initial characteristics of calibrated microvesicles, as characterized before the lyophilization process, resulting suitable for subsequent pharmaceutical uses.

Said reconstituted suspension of calibrated microvesicles is characterized by calibrated microvesicles having a GSD of at least 1.2 or lower, preferably of at least 1.15, down to e.g. 1.1.

In an embodiment of this invention, said reconstituted suspension of calibrated microvesicles is characterized by a concentration of at least $2.0 \times 10^8$ CMV/mL, preferably $2.25 \times 10^8$ CMV/mL, more preferably $2.5 \times 10^8$ CMV/mL, up to $5.50 \times 10^8$ CMV/mL.

As indicated above, the expression "microvesicles concentration" refers to the number of microvesicles in a volume unit, determined using a Coulter Counter apparatus, i.e. number of MB/mL.

Typically, the concentration of calibrated microvesicles (%), measured after the reconstitution of the freeze-dried composition of the invention with suitable aqueous solution, allows to determine the microbubble yield after said reconstitution, in comparison to the microvesicles concentration measured before the freeze-drying process.

In the present invention, the calibrated microvesicles yield after the reconstitution of the freeze-dried composition of the invention is at least 50%, preferably at least 55%, more preferably at least 60% even more preferably at least 65%, up to e.g. 85%, preferably 90%, more preferably 95%, even more preferably 100%.

The expression "calibrated microvesicles yield" refers to the ratio between the microvesicles concentration measured before freeze-drying and the microvesicles concentration measured after freeze-drying and redispersion (see Equation 2):

$$\text{CMV yield after freeze-drying (\%)} = (\text{CMV concentration after freeze-drying/mL})/(\text{CMV concentration before freeze-drying/mL}) \qquad \text{Eq.2:}$$

The expression "GSD ratio" indicates the ratio of the GSD value measured to CMV before freeze drying over the GSD value after freeze drying (see Equation 3):

$$\text{GSD ratio} = (\text{GSD before freeze-drying})/(\text{GSD after freeze drying}) \qquad \text{Eq.3:}$$

The monodispersity of a CMV system after the freeze-drying process can be monitored through the GSD ratio value. For instance, a good monodispersity is assessed when the GSD value after freeze-drying is similar to t the one before freeze-drying, resulting in a GSD ratio close to 1. Generally, higher GSD ratios (i.e. closer to 1) indicate a preservation of the initial monodispersity in the CMV distribution after freeze-drying.

Use

The microvesicles prepared according to the method of the invention may be used in a variety of diagnostic and/or therapeutic techniques, including in particular Ultrasound and Magnetic Resonance.

Diagnostic methods include any method where the use of the gas-filled microvesicles allows enhancing the visualisation of a portion or of a part of an animal (including humans) body, including imaging for preclinical and clinical research purposes. A variety of imaging techniques may be employed in ultrasound applications, for example including fundamental and harmonic B-mode imaging, pulse or phase inversion imaging and fundamental and harmonic Doppler imaging; if desired three-dimensional imaging techniques may be used.

Microvesicles according to the invention may typically be administered in a concentration of from about 0.01 to about 1.0 µL of gas per kg of patient, depending e.g. on their respective composition, the tissue or organ to be imaged and/or the chosen imaging technique. This general concentration range may of course vary depending on specific imaging applications, e.g. when signals can be observed at very low doses such as in colour Doppler or power pulse inversion.

In an embodiment said method of diagnosing comprises
(i) administering to a patient a suspension of gas-filled microvesicles obtained by reconstitution of a freeze-dried product obtained according to the process of the invention; and
(ii) detecting an ultrasound signal from a region of interest in said patient.

According to an embodiment, said suspension of gas-filled microvesicles comprises an amphiphilic material and a mixture of freeze-drying protecting component.

Reconstitution of the freeze-dried product is preferably made by dispersing it into a physiologically acceptable aqueous carrier, e.g. saline, in the presence of a physiologically acceptable gas, e.g $SF_6$, under gentle agitation.

Possible other diagnostic imaging applications include scintigraphy, light imaging, and X-ray imaging, including X-ray phase contrast imaging.

Another aspect of the invention relates to the use in a method of therapeutic treatment of a suspension of microvesicles reconstituted from freeze-dried product according to the invention.

Therapeutic techniques include any method of treatment (as above defined) of a patient which comprises the combined use of ultrasounds and gas-filled microvesicles either as such (e.g. in ultrasound mediated thrombolysis, high intensity focused ultrasound ablation, blood-brain barrier permeabilization, immunomodulation, neuromodulation, radiosensitization) or in combination with a therapeutic agent (i.e. ultrasound mediated delivery, e.g. for the delivery of a drug or bioactive compound to a selected site or tissue, such as in tumor treatment, gene therapy, infectious diseases therapy, metabolic diseases therapy, chronic diseases therapy, degenerative diseases therapy, inflammatory diseases therapy, immunologic or autoimmune diseases therapy or in the use as vaccine), whereby the presence of the gas-filled microvesicles may provide a therapeutic effect itself or is capable of enhancing the therapeutic effects of the applied ultrasounds, e.g. by exerting or being responsible to exert a biological effect in vitro and/or in vivo, either by itself or upon specific activation by various physical methods (including e.g. ultrasound mediated delivery).

Microvesicles according to the invention can typically be administered for therapeutic purposes in a concentration of from about 0.01 to about 5.0 µL of gas per kg of patient, depending e.g. from their respective composition, the type of subject under treatment, the tissue or organ to be treated and/or the therapeutic method applied.

In an embodiment said method of ultrasound therapeutic treatment comprises:
(i) administering to a patient a suspension of gas-filled microvesicles obtained by reconstitution of a freeze-dried product obtained according to the process of the invention;
(ii) identifying a region of interest in said patient to be submitted to a therapeutic treatment, said region of interest comprising said suspension of gas-filled microvesicles; and
(iii) applying an ultrasound beam for therapeutically treating said region of interest;
whereby said ultrasound therapeutic treatment is enhanced by the presence of said suspension of gas-filled microvesicles in said region of interest.

The following examples will help to further illustrate the invention.

EXAMPLES

Example 1

Preparation of Gas-Filled Microvesicles

Gas-filled microvesicles were synthesized using a commercially available microfluidic flow-focusing device (CU4553.007 N30 design, Micronit Microfluidics, NL), mounted in a commercially available chip holder (Micronit microfluidics, Fluidic Connect PRO Chip Holder with 4515 Inserts). The microvesicles formation channel had a width of 19 µm. The chip and its holder were positioned in an optically transparent temperature controlled water bath that was mounted on an inverted microscope equipped with a 20 times magnification objective (Olympus, LMPLAN 20×) and a CCD camera (Lumenera, LM156M). The temperature of the thermostatic bath was set at 50° C.

The amphiphilic materials in the liquid flow were: DSPC: DPPE-PEG5000 in a respective molar ratio of 9:1.

The materials were added with the above molar ratios at a concentration of 20 mg/mL to a 2:1 (volume ratio) chloroform/methanol mixture under stirring at 60° C. until complete dissolution the amphiphilic material. The solvent was then evaporated under reduced pressure and the obtained film was dried overnight under reduced pressure. The dried material was then redispersed (at concentrations of 15 mg/mL) in saline (0.9% NaCl) at 60° C. under stirring for 30 minutes. The dispersion was then sonicated by using a tip sonicator (Branson Sonifier 250) to homogenously disperse the material. The preparations were then filtered using a polycarbonate filter (0.45 µm pore size), cooled down to room temperature and degassed.

Gas-filled microvesicles comprising $CO_2/C_4F_{10}$ in a volume ratio of 85/15 were prepared with a gas-mixing device similar to the one schematically illustrated in FIG. 3. Briefly, two gas containers were filled with $CO_2$ and $C_4F_{10}$, respectively. The gas flow of each gas was regulated by respective mass flow controllers: (i) EL-Flow: F200CV-002-RAD-11-K, for the $CO_2$ and (ii) Low-$\Delta$P-Flow: F-200DV-RAD-11-Z for $C_4F_{10}$ (both gas controllers from Bronkhorst, Ruurlo, The Netherlands). The mass flow controllers were controlled by a customized software program implemented in Matlab (Mathworks), which was installed on a personal computer, in order to set and keep the desired mixing ratio. A pressure sensor (PSE530-M5-L; SMC Corp., Tokyo, Japan) measured the actual pressure in the gas mixture in the outlet channel leading to the microfluidic chip; a gas pressure of 2 bars was used for the formation of the microvesicles. The liquid co-flow rate was controlled by using a separate mass flow controller (Mini Cori Flow: M13V14I-MAD-11-K-S; Bronkhorst, Ruurlo, The Netherlands). A liquid co-flow rate of around 150 µL/min was used to operate the flow-focusing device in the jetting regime and produce microvesicles with a diameter (mode) of around 4 µm.

Example 2

Preparation of the Freeze-Dried Composition

Firstly, 3 mL of the calibrated microvesicles suspension obtained through the microfluidic flow-focusing method, as described in Example 1, were transferred in a Pyrex tube (Pyrex disposable tube 12×75 mm) without further addition of $C_4F_{10}$ in the tube. Then, the calibrated microvesicles suspension was centrifuged (Sigma 3-16 Centrifuge) for 6 minutes at 64 g, and the infranatant was withdrawn by means of a syringe equipped with a needle. The remaining 200 µL of washed microvesicles were redispersed with 3 mL of a solution comprising the freeze-drying protecting components as detailed in the following examples. The effective concentration of freeze-drying protecting components was 188 mg/mL after redispersion of the remaining washed microvesicles.

The calibrated microvesicles suspended in the solution of freeze-drying protecting components were then aliquoted in DINER glass vials (1.5 mL suspension/vial) and transferred in the freeze dryer.

The vials were cooled at temperatures between −30° C. and −60° C. (as detailed in the subsequent examples) and freeze-dried for approximately 1 hour under vacuum. At the end of the procedure, a freeze-dried composition was obtained as a white homogenous dry solid. The head space was then filled with pure $C_4F_{10}$.

Example 3

Effect of the Freeze-Drying Protecting Components on Calibrated Microvesicles Characteristics Table 1 lists the freeze-drying protecting components which were investigated.

TABLE 1

| Selected freeze-drying protecting components, classified by chemical class | | |
|---|---|---|
| Molecule | Class | Molecular Weight (g/mol) |
| PEG4000 | Polymer | 4'000 |
| PEG8000 | Polymer | 8'000 |
| Xylitol | Polyol | 152.2 |
| Sorbitol | Polyol | 182.2 |
| Mannitol | Polyol | 182.2 |
| Glucose | Monosaccharide | 180.2 |
| Maltose | Disaccharide | 342.3 |
| Sucrose | Disaccharide | 342.3 |
| Dextran 6000 | Polysaccharide | 6'000 |

The above materials were used either as single components or as mixtures thereof, at various concentrations, in the preparation of the freeze-dried composition illustrated in example 2 at a temperature of −60° C. Table 2 lists the various examples of the single components (S1-513) and of the mixtures thereof (M1-M9).

TABLE 2

| Composition and concentration of solutions of freeze-drying protecting components | | |
|---|---|---|
| Prep No. | Freeze-drying protecting components | Total concentration of the freeze-drying protecting components (mg/mL) |
| S1A | PEG4000 | 100 |
| S2A | PEG8000 | 100 |
| S3A | Sorbitol | 100 |
| S4 | Xylitol | 100 |
| S5 | Mannitol | 100 |
| M1 (S1A + S3A) | PEG4000 + Sorbitol | 200 |
| M2 (S2A + S3A) | PEG8000 + Sorbitol | 200 |
| M9 (S1A + S4) | PEG4000 + Xilitol | 200 |
| M3 (S2A + S4) | PEG8000 + Xylitol | 200 |
| M4 (S2A + S5) | PEG8000 + Mannitol | 200 |
| S6 | Sucrose | 100 |
| S7A | Maltose | 100 |
| S8 | Raffinose | 100 |
| S9 | Dextran 6000 | 100 |
| M5 (S2A + S6) | PEG8000 + Sucrose | 200 |
| M6 (S2A + S7A) | PEG8000 + Maltose | 200 |
| M7 (S2A + S8) | PEG8000 + Raffinose | 200 |
| M8 (S2A + S9) | PEG8000 + Dextran 6000 | 200 |

Characterization

After the freeze-drying process, each freeze-dried composition was reconstituted with 1.5 mL of aqueous solution in the presence of a biocompatible gas, in order to obtain a calibrated and stable microvesicles suspension. The concentration of the mixture of freeze-drying protecting components was 188 mg/mL, before and after freeze drying.

After reconstitution, the reconstituted calibrated microvesicles suspensions were let 5 min on the bench before being characterized using a Coulter Counter Multisizer 3 fitted with a 30 µm aperture tube, to measure the size, the geometric standard deviation (GSD), the concentration of microvesicles and the yield after the freeze-drying process. Results The main results of the characterization of the reconstituted calibrated microvesicles suspensions are reported in Table 3 and Table 4.

The GSD value and the concentration of microvesicles were measured before and after the freeze-drying process to evaluate the efficacy of the freeze-drying protecting components in preserving the initial characteristics of the calibrated microvesicles.

Considering the GSD value and the microvesicles yield after freeze-drying, results clearly show that adding a mixture of freeze-drying protecting components to the calibrated microvesicles suspension is more effective than the addition of a single component in preserving the microvesicles characteristics.

TABLE 3

| GSD, CMV yield and concentration of calibrated vesicles suspensions obtained after reconstitution of lyophilized compositions comprising a single freeze-drying protecting component (FD = freeze-drying). | | | |
|---|---|---|---|
| Prep No. | Total concentration of the freeze-drying protecting components (mg/mL) | GSD | CMV Yield after FD (2-6 µm) (%) | Concentration (CMV/mL) |
| S1A | 100 | 1.20 | 39 | $1.6 \times 10^8$ |
| S2A | 100 | 1.21 | 26 | $0.9 \times 10^8$ |

TABLE 3-continued

| | GSD, CMV yield and concentration of calibrated vesicles suspensions obtained after reconstitution of lyophilized compositions comprising a single freeze-drying protecting component (FD = freeze-drying). | | | |
|---|---|---|---|---|
| Prep No. | Total concentration of the freeze-drying protecting components (mg/mL) | GSD | CMV Yield after FD (2-6 µm) (%) | Concentration (CMV/mL) |
| S3A | 100 | 1.33 | 3 | $0.1 \times 10^8$ |
| S4 | 100 | 1.34 | 8 | $0.3 \times 10^8$ |
| S5 | 100 | 1.34 | 14 | $0.5 \times 10^8$ |
| S6 | 100 | 1.28 | 13 | $0.4 \times 10^8$ |
| S7A | 100 | 1.28 | 22 | $1.0 \times 10^8$ |
| S8 | 100 | 1.22 | 23 | $0.9 \times 10^8$ |
| S9 | 100 | 1.26 | 21 | $0.8 \times 10^8$ |

From the results displayed in Table 4, it is evident that the freeze-drying efficiency was improved using a mixture of freeze-drying protecting components. In particular, freeze-drying of calibrated microvesicles in mixtures of polyethylene glycols (PEG4000 and PEG8000) and polyols (i.e. xylitol, sorbitol, and mannitol) enabled to improve the microvesicles yield after freeze-drying. For instance, the use of the mixtures M1 allowed an increase of 17% of the microvesicles yield after freeze-drying, compared to the use of S1A. Still more advantageously, the use of M2 enabled a higher increase of the CMV yield of 38%, compared to the formulation S2A. Moreover, freeze-drying the CMV in the mixture M2 allowed to obtain a better GSD value of 1.17, lower than those obtained using the single freeze-drying protecting component of the formulations S2A and S3A, 1.21 and 1.33, respectively.

The same trend was observed after freeze-drying calibrated microvesicles in mixtures of polyethylene glycols (PEG4000 and PEG8000) and saccharides (i.e. maltose, sucrose, raffinose, Dextran6000). For instance, the CMV yield after freeze-drying in the mixture M5 was found to be 51%, with an increase of 25% when compared to formulation S2A. Moreover, also the GSD value using the mixture M5 was found to be 1.17, remarkably lower than the single freeze-drying protecting component, S2A and S6, 1.21 and 1.28 respectively.

TABLE 4

| | GSD, CMV yield and concentration of calibrated vesicles suspensions obtained after reconstitution of lyophilized compositions comprising a mixture of freeze-drying protecting components (FD = freeze-drying). | | | |
|---|---|---|---|---|
| Prep No. | Total concentration of the freeze-drying protecting components (mg/mL) | GSD | CMV Yield after FD (2-6 µm) (%) | Concentration (CMV/mL) |
| M1 (S1A + S3A) | 200 | 1.20 | 56 | $2.2 \times 10^8$ |
| M2 (S2A + S3A) | 200 | 1.17 | 64 | $2.3 \times 10^8$ |
| M3 (S2A + S4) | 200 | 1.16 | 64 | $2.4 \times 10^8$ |
| M4 (S2A + S5) | 200 | 1.22 | 52 | $1.8 \times 10^8$ |
| M5 (S2A + S6) | 200 | 1.17 | 51 | $1.8 \times 10^8$ |
| M6 (S2A + S7A) | 200 | 1.18 | 51 | $1.6 \times 10^8$ |

TABLE 4-continued

| | GSD, CMV yield and concentration of calibrated vesicles suspensions obtained after reconstitution of lyophilized compositions comprising a mixture of freeze-drying protecting components (FD = freeze-drying). | | | |
|---|---|---|---|---|
| Prep No. | Total concentration of the freeze-drying protecting components (mg/mL) | GSD | CMV Yield after FD (2-6 µm) (%) | Concentration (CMV/mL) |
| M7 (S2A + S8) | 200 | 1.26 | 43 | $1.4 \times 10^8$ |
| M8 (S2A + S9) | 200 | 1.23 | 41 | $1.6 \times 10^8$ |
| M9 (S1A + S4) | 200 | 1.18 | 68 | $2.2 \times 10^8$ |

Example 4

Characterization of the Calibrated Microvesicles Characteristics after Freeze-Drying at Different Freezing Temperatures The preparation of the freeze-dried composition was furtherly investigated evaluating different freezing temperatures at which the freshly-prepared calibrated microvesicles are cooled at the beginning of the lyophilization procedure.

The preparation process was performed as previously described in Example 2, except that the vials were cooled at different freezing temperatures, as reported in Table 5.

At the end of the freeze-drying process, each lyophilized composition was reconstituted with 1.5 mL of aqueous solution in the presence of a biocompatible gas, in order to obtain a calibrated and stable microvesicles suspension. The freeze-dried composition is thus reconstituted with a volume of aqueous solution similar to the volume of suspension which underwent the freeze-drying process. Accordingly, the concentration of the freeze-drying protecting components in the reconstituted suspension is substantially the same as the one in the initial suspension.

After reconstitution, the reconstituted calibrated microvesicles suspensions were let 5 min on the bench before being characterized using a Coulter Counter Multisizer 3 fitted with a 30 µm aperture tube, to measure the size, the geometric standard deviation (GSD), the concentration of microvesicles and the yield after the freeze-drying process.

Table 5 reports the GSD value and the microvesicles yield measured after freeze-drying for each microvesicles suspension obtained after reconstitution of lyophilized compositions frozen at different temperatures and comprising different freeze-drying protecting components.

Results

Results confirmed that the use of mixtures of freeze-drying components allows to improve the freeze-drying performance at any investigated freezing temperature, when compared with the use of single components. For instance, as displayed in Table 5, the CMV freeze-dried in the mixture M2 were characterized by the lowest GSD values at any investigated freezing temperature, confirming the results previously obtained in the Example 3.

TABLE 5

| | GSD value, CMV yield and concentration of CMV measured after freeze-drying (FD) at different freezing temperatures. | | | | |
|---|---|---|---|---|---|
| Prep No. | FD protecting components (mg/mL) | Freezing T° (° C.) | GSD | CMV Yield after FD (2-6 μm) (%) | Concentration (CMV/mL) |
| M2 | PEG8000 + | −60° C. | 1.16 | 64 | $2.3 \times 10^8$ |
| (S2A + S3A) | Sorbitol | −50° C. | 1.18 | 67 | $2.6 \times 10^8$ |
| | (200 mg/mL) | −40° C. | 1.175 | 67 | $2.8 \times 10^8$ |
| | | −30° C. | 1.16 | 62 | $2.6 \times 10^8$ |
| M3 | PEG8000 + | −60° C. | 1.17 | 64 | $2.4 \times 10^8$ |
| (S2A + S4) | Xylitol | −50° C. | 1.17 | 66 | $2.4 \times 10^8$ |
| | (200 mg/mL) | −40° C. | 1.17 | 66 | $3.0 \times 10^8$ |
| | | −30° C. | 1.19 | 54 | $2.4 \times 10^8$ |
| M6 | PEG8000 + | −60° C. | 1.18 | 51 | $1.6 \times 10^8$ |
| (S2A + S7A) | Maltose | −50° C. | 1.18 | 58 | $1.8 \times 10^8$ |
| | (200 mg/mL) | −40° C. | 1.20 | 63 | $2.9 \times 10^8$ |
| | | −30° C. | 1.18 | 43 | $2.0 \times 10^8$ |

Example 5

Effect of the Concentration of the Freeze-Drying Protecting Components on Calibrated Microvesicles Characteristics The concentration of the freeze-drying protecting components mixture was also investigated in order to evaluate the freeze-drying efficiency, in terms of preservation of GSD value and microvesicles yield after freeze-drying.

For this study, mixtures of freeze-drying protecting components were compared with the corresponding freeze-drying protecting component alone. In particular, the following freeze-drying protecting components were evaluated:

i) PEG4000 and sorbitol (contained in equal amount) compared with PEG4000 alone.

ii) PEG4000 and xylitol (contained in equal amount) compared with PEG4000 alone.

iii) PEG8000 and sorbitol (contained in equal amount) compared with PEG8000 alone.

iv) PEG8000 and xylitol (contained in equal amount) compared with PEG8000 alone.

Different solutions in a range of concentrations between 50 mg/ml and 250 mg/ml were prepared for each investigated formulation.

The calibrated microvesicles suspended in the different solutions of freeze-drying protecting components were then aliquoted in DINER glass vials (1.5 mL suspension/vial) and transferred in the freeze dryer.

The vials were cooled at −60° C. or −40° C. (PEG8000 mixtures) and −60° C. (PEG4000 mixtures) for 1 hour at ambient pressure, and followed by primary drying at −20° C. and 0.1 mbar. At the end of the procedure, a freeze-dried composition was obtained as a white homogenous dry solid. The headspace was then filled with pure $C_4F_{10}$.

Results

The CMV yield after freeze-drying (Equation 2) and the GSD ratio (Equation 3) were taken into consideration to study the effect of the concentration of the freeze-drying protecting components on calibrated microvesicles characteristics.

i) PEG4000 and Sorbitol (Contained in Equal Amount) Compared with PEG4000 Alone.

Table 6 reports the comparison between the CMV yield after freeze-drying and the GSD ratio for the FD protecting mixture PEG4000 and sorbitol and the PEG4000 alone at increasing concentrations.

Considering the CMV yield, results showed that an increasing improvement of the freeze-drying efficiency was obtained using concentrations of freeze-drying protecting components between 50 mg/mL and 200 mg/mL for both the mixture and the single components. Moreover, results showed that substantially similar CMV yields are obtained for the mixture PEG4000 and sorbitol and the PEG4000 alone at the investigated freezing temperature (200 mg/ml).

On the contrary, as far as the GSD ratio is concerned, a difference between the single component and the mixture was observed. Particularly, when freezing at −60° C., GSD ratios resulted in systematically increased values for the PEG4000 and sorbitol mixture than for the PEG4000 alone.

TABLE 6

| | | | Comparison between PEG4000 alone (S1A) and PEG 4000 + sorbitol mixture (M1) | | |
|---|---|---|---|---|---|
| FD protecting components concentration (mg/mL) | Freezing T° | CMV Yield after FD | | GSD ratio | |
| | | PEG4000 | PEG4000 + Sorbitol | PEG4000 | PEG4000 + Sorbitol |
| 50 | −60° C. | 18% | 28% | 0.879 | 0.894 |
| 100 | −60° C. | 42% | 47% | 0.887 | 0.896 |
| 150 | −60° C. | 69% | 58% | 0.894 | 0.906 |
| 200 | −60° C. | 65% | 65% | 0.887 | 0.899 |
| 250 | −60° C. | 65% | 70% | 0.897 | 0.910 | ii) PEG4000 and Xylitol (Contained in Equal Amount) Compared with PEG4000 Alone.

Table 7 reports the comparison between the CMV yield after freeze-drying and the GSD ratio for the FD protecting PEG4000 and xylitol mixture and the PEG4000 alone at increasing concentrations.

However, at the freezing temperature of −60° C., CMV yields were found to be increased only for the mixture at low concentration (50-100 mg/mL) while the values are substantially similar at higher concentration (especially 200 mg/mL) for both the mixture and the single component.

TABLE 7

| Comparison between PEG4000 alone (S1A) and PEG 4000 + xylitol mixture (M9) | | | | | |
|---|---|---|---|---|---|
| FD protecting components concentration | Freezing | CMV Yield after FD | | GSD ratio | |
| (mg/mL) | T° | PEG4000 | PEG4000 + Xilitol | PEG4000 | PEG4000 + Xilitol |
| 50 | −60° C. | 18% | 44% | 0.879 | 0.900 |
| 100 | −60° C. | 42% | 53% | 0.887 | 0.926 |
| 150 | −60° C. | 69% | 55% | 0.894 | 0.926 |
| 200 | −60° C. | 65% | 66% | 0.887 | 0.932 |
| 250 | −60° C. | 65% | 61% | 0.897 | 0.922 |

Similarly to the previous (case i), results related to the GSD ratio showed an improved freeze-dried efficiency of the PEG4000 and xylitol mixture when freezing at −60° C., resulting in better GSD ratios values than for the PEG4000 alone. Differently, CMV yields were found to be higher for the mixture only at low concentration (50-100 mg/mL).

iii) PEG8000 and Sorbitol (Contained in Equal Amount) Compared with PEG8000 Alone Table 8 reports the comparison between the CMV yield after freeze-drying and the GSD ratio for each investigated concentration by comparing the formulations containing the mixture of PEG8000 and sorbitol and that containing PEG8000 alone.

Differently, at the freezing temperature of −40° C. the mixture PEG8000 and sorbitol displayed improved values of both CMV yield and GSD ratio compared to the PEG8000 alone.

As displayed in Table 8, the advantageous use of the mixture of PEG8000 and sorbitol instead of PEG8000 alone was also confirmed by the GSD ratio value. Particularly, higher GSD values were assessed when CMV were freeze-dried in a solution of PEG8000 and sorbitol at all the tested concentrations and at both the freezing temperatures, demonstrating an improved monodispersity in comparison with the CMV suspension containing an equal amount of PEG8000.

TABLE 8

| Comparison between PEG8000 alone (S2A) and PEG 8000 + sorbitol mixture (M2) | | | | | |
|---|---|---|---|---|---|
| FD protecting components concentration | Freezing | CMV Yield after FD | | GSD Ratio | |
| (mg/mL) | T° | PEG8000 | PEG8000 + Sorbitol | PEG8000 | PEG8000 + Sorbitol |
| 50 | −40° C. | 15% | 23% | 0.869 | 0.892 |
|  | −60° C. | 5% | 23% | 0.864 | 0.885 |
| 100 | −40° C. | 29% | 47% | 0.886 | 0.914 |
|  | −60° C. | 30% | 41% | 0.895 | 0.902 |
| 150 | −40° C. | 50% | 62% | 0.89 | 0.92 |
|  | −60° C. | 56% | 54% | 0.898 | 0.906 |
| 200 | −40° C. | 56% | 67% | 0.896 | 0.920 |
|  | −60° C. | 57% | 59% | 0.900 | 0.914 |
| 250 | −40° C. | 58% | 70% | 0.892 | 0.916 |
|  | −60° C. | 59% | 71% | 0.894 | 0.928 |

Considering the CMV yield, results showed that an increasing improvement of the freeze-drying efficiency was obtained using concentrations of freeze-drying protecting components between 50 mg/mL and 250 mg/mL for both the mixture and the single components at both the freezing temperatures.

v) PEG8000 and Xylitol (Contained in Equal Amount) Compared with PEG8000 Alone

Table 9 reports the comparison between the CMV yield after freeze-drying and the GSD ratio for each investigated concentration by comparing the formulations containing the PEG8000 and xylitol mixture and that containing PEG8000 alone.

TABLE 9

| Comparison between PEG8000 alone (S2A) and PEG 8000 + Xilitol mixture (M3) | | | | | |
|---|---|---|---|---|---|
| FD protecting components concentration | Freezing | CMV Yield after FD | | GSD ratio | |
| (mg/mL) | T° | PEG8000 | PEG8000 + Xilitol | PEG8000 | PEG8000 + Xilitol |
| 50 | −40° C. | 15% | 26% | 0.869 | 0.891 |
| | −60° C. | 5% | 32% | 0.864 | 0.918 |
| 100 | −40° C. | 29% | 46% | 0.886 | 0.905 |
| | −60° C. | 30% | 47% | 0.895 | 0.926 |
| 150 | −40° C. | 50% | 56% | 0.89 | 0.912 |
| | −60° C. | 56% | 57% | 0.898 | 0.938 |
| 200 | −40° C. | 56% | 67% | 0.896 | 0.915 |
| | −60° C. | 57% | 63% | 0.900 | 0.941 |
| 250 | −40° C. | 58% | 67% | 0.892 | 0.913 |
| | −60° C. | 59% | 64% | 0.894 | 0.946 |

As demonstrated from the increasing CMV yield values, an improvement of the freeze-drying efficiency was obtained using concentrations of freeze-drying protecting components between 50 mg/mL and 250 mg/mL for both the mixture and the single components. Results showed that at the freezing temperature of −60° C., CMV yield values are particularly improved for the mixture at low concentrations <100 mg/mL.

GSD ratios were found to be improved in the mixture at all concentrations and at both freezing temperatures.

Analogously to the case iii), at the freezing temperature of −40° C. the PEG8000 and xylitol mixture displayed improved values of both CMV yield and GSD ratio compared to the PEG8000 alone, confirming its improved freeze-dried efficiency.

From the analysis of the overall results emerged the use of the mixtures of FD protecting components endows to an increased improvement of the freeze-drying efficiency when compared to the single FD protecting component.

Particularly, comparing S1A with M1 (PEG4000+Sorbitol) and M9 (PEG4000+xylitol) was observed that improved GDS ratio values were assessed for the mixtures when freezing at −60° C.

From the comparison between S2A (PEG8000) with the mixture M2 (PEG8000+Sorbitol) and M3 (PEG8000+Xylitol) emerged that an increasing improvement of the freeze-drying efficiency of the mixtures was assessed when freezing at −40° C., where an increase of all the investigated parameters (CMV yield, GSD, GSD ratios) was observed. However, at a freezing temperature of −60° C., while CMV yields were found to be similar or slightly higher for the mixtures compared to the single FD protecting component, only the GSD ratios and GSD values resulted improved for the mixtures M2 and M3, particularly at high concentration of cryoprotectant (≥200 mg/mL).

CITED REFERENCES

1. WO2018/041906 A1—BRACCO SUISSE SA
2. PCT application number PCT/EP2019/055325
3. US2017/080113 A1—GE Healthcare
4. WO97/29782 A1—NICOMED IMAGING A/S

The invention claimed is:

1. A freeze-dried composition comprising i) an amphiphilic material comprising a phospholipid and ii) a freeze-drying protecting component which, upon reconstitution with a pharmaceutically acceptable solution in the presence of a biocompatible gas, is capable of providing a suspension of calibrated gas-filled microvesicles having a geometric standard deviation (GSD) of 1.2 or lower, wherein said freeze-drying protecting component is a mixture of at least two freeze-drying protecting components comprising: (a) a polyethylene glycol, wherein said polyethylene glycol has a molecular weight from 4000 to 8000 g/mol, and (b) a polyol, wherein said polyol is sorbitol or xylitol.

2. A suspension of gas-filled microvesicles obtained by reconstituting a freeze-dried composition according to claim 1 with a pharmaceutically acceptable solution in the presence of a biocompatible gas, wherein said suspension has a geometric standard deviation (GSD) of 1.2 or lower.

3. The suspension of gas-filled microvesicles according to claim 2, wherein said suspension comprises the mixture of at least two freeze-drying protecting components at a concentration between 10 and 25% (w/v %).

4. The suspension of gas-filled microvesicles according to claim 2, wherein said suspension is characterized by a concentration of from $2.5 \times 10^8$ to $5.5 \times 10^8$ microvesicles/mL.

5. A method of preparing a freeze-dried composition for the preparation of a reconstituted suspension of calibrated gas-filled microvesicles, comprising the steps of:
   a. preparing a suspension of calibrated gas-filled microvesicles comprising i) an amphiphilic material comprising a phospholipid and ii) a mixture of at least two freeze-drying protecting components comprising: (a) a polyethylene glycol, wherein said polyethylene glycol has a molecular weight from 4000 to 8000 g/mol, and (b) a polyol, wherein said polyol is sorbitol or xylitol; and
   b. freeze-drying the calibrated microvesicles suspension.

6. The method of claim 5, wherein the method of preparation of step a. comprises a microfluidic flow-focusing technique.

7. The method of claim 5, wherein said mixture of freeze-drying protecting components has a total concentration comprised between 100 mg/ml and 300 mg/mL.

8. A process for the preparation of an injectable contrast agent comprising a suspension of gas-filled microvesicles, wherein said process comprises reconstituting a freeze-dried composition as defined in claim 1, with a pharmaceutically acceptable solution in the presence of a biocompatible gas, wherein said suspension has a geometric standard deviation (GSD) of 1.2 or lower.

9. The method of claim 5, wherein said mixture of freeze-drying protecting components has a total concentration comprised between 120 mg/mL and 250 mg/mL.

10. The method of claim 5, wherein said mixture of freeze-drying protecting components has a total concentration of 200 mg/mL.

11. The freeze-dried composition according to claim 1, wherein said mixture of at least two freeze-drying protecting components has a total concentration from 50 mg/mL to 100 mg/mL.

12. The freeze-dried composition according to claim 1, wherein said mixture of at least two freeze-drying protecting components has a total concentration of 100 mg/mL.

13. The suspension of gas-filled microvesicles according to claim 2, wherein said suspension is characterized by a concentration of from $2.0 \times 10^8$ to $5.5 \times 10^8$ microvesicles/mL.

14. The method of claim 5, wherein said mixture of freeze-drying protecting components has a total concentration from 50 mg/mL to 100 mg/mL.

15. The method of claim 5, wherein said mixture of freeze-drying protecting components has a total concentration of 100 mg/mL.

16. The process according to claim 8, wherein said suspension is characterized by a concentration of from $2.0 \times 10^8$ to $5.5 \times 10^8$ microvesicles/mL.

17. The process according to claim 8, wherein said suspension is characterized by a concentration of from $2.5 \times 10^8$ to $5.5 \times 10^8$ microvesicles/mL.

\*    \*    \*    \*    \*